United States Patent
Bergström et al.

(10) Patent No.: US 6,572,766 B1
(45) Date of Patent: Jun. 3, 2003

(54) MATRICES FOR SEPARATION AND SEPARATION EXPLOITING SAID MATRICES

(75) Inventors: Jan Bergström, Bälinge (SE); Rolf Berglund, Uppsala (SE); Lennart Söderberg, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 09/380,050

(22) PCT Filed: Mar. 4, 1998

(86) PCT No.: PCT/SE98/00387

§ 371 (c)(1),
(2), (4) Date: Jan. 24, 2000

(87) PCT Pub. No.: WO98/39094

PCT Pub. Date: Sep. 11, 1998

(30) Foreign Application Priority Data

Mar. 4, 1997 (SE) ................................................ 9700769

(51) Int. Cl.⁷ .............................................. B01D 15/08
(52) U.S. Cl. ............................... 210/198.2; 210/502.1; 210/635; 210/656; 502/404
(58) Field of Search ................... 210/635, 656, 210/198.2, 502.1; 502/401, 402, 404

(56) References Cited

U.S. PATENT DOCUMENTS

| | | | | |
|---|---|---|---|---|
| 3,959,251 A | | 5/1976 | Porath et al. ............. 210/198.2 |
| 4,352,884 A | * | 10/1982 | Nakashima et al. ...... 210/198.2 |
| 4,415,631 A | * | 11/1983 | Schutijser ................. 210/198.2 |
| 4,535,010 A | * | 8/1985 | Axen ........................... 427/246 |
| 4,544,485 A | | 10/1985 | Pinkerton et al. ......... 210/502.1 |
| 4,647,655 A | | 3/1987 | Axen et al. .................. 530/390 |
| 4,673,734 A | * | 6/1987 | Tayot .......................... 210/656 |
| 4,746,572 A | * | 5/1988 | Glajch ...................... 210/198.2 |
| 4,871,711 A | * | 10/1989 | Matin ....................... 210/198.2 |
| 5,030,352 A | | 7/1991 | Varady et al. ............ 210/198.2 |
| 5,128,291 A | * | 7/1992 | Wax ......................... 210/198.2 |
| 5,139,881 A | * | 8/1992 | Henis .......................... 424/488 |
| 5,522,994 A | | 6/1996 | Frechet et al. ........... 210/198.2 |
| 5,593,729 A | * | 1/1997 | Frechet ....................... 427/337 |
| 5,633,290 A | * | 5/1997 | Frechet ........................ 521/54 |
| 5,653,875 A | * | 8/1997 | Betz ......................... 210/198.2 |
| 6,045,697 A | * | 4/2000 | Girot ....................... 210/198.2 |

FOREIGN PATENT DOCUMENTS

| | | | |
|---|---|---|---|
| EP | 0 165 912 | 12/1985 | .............. 210/198.2 |
| EP | 0 168 363 | 1/1986 | .............. 210/198.2 |
| EP | 0 221 046 | 5/1987 | .............. 210/198.2 |
| WO | WO 91/00762 | 1/1991 | .............. 210/198.2 |
| WO | WO 91/18237 | 11/1991 | .............. 210/198.2 |
| WO | WO 92/00799 | 1/1992 | .............. 210/198.2 |
| WO | WO 92/18237 | 10/1992 | .............. 210/198.2 |
| WO | WO 93/17055 | 9/1993 | .............. 210/198.2 |
| WO | WO 93/19115 | 9/1993 | .............. 210/198.2 |
| WO | WO 94/08686 | 4/1994 | .............. 210/198.2 |
| WO | WO 94/09063 | 4/1994 | .............. 210/198.2 |
| WO | WO 95/33557 | 12/1995 | .............. 210/198.2 |
| WO | WO 97/29825 | 8/1997 | .............. 210/198.2 |
| WO | WO 98/39364 | 9/1998 | .............. 210/198.2 |

OTHER PUBLICATIONS

J. Porath, et al., "Agar Derivatives for Chromatography, Electrophoresis and Gel–Bound Enzymes", Journal of Chromatography, 60, 1971, pp. 167–177.

* cited by examiner

Primary Examiner—Ernest G. Therkorn
(74) Attorney, Agent, or Firm—Royal N. Ronning, Jr.; Stephen G. Ryan

(57) ABSTRACT

A matrix is disclosed including a core showing a system of micropores and a surface in which the micropore system has openings. The characterizing feature is that the surface is coated with a polymer (I) having such a large molecular weight that it cannot penetrate into the micropores.

23 Claims, 3 Drawing Sheets

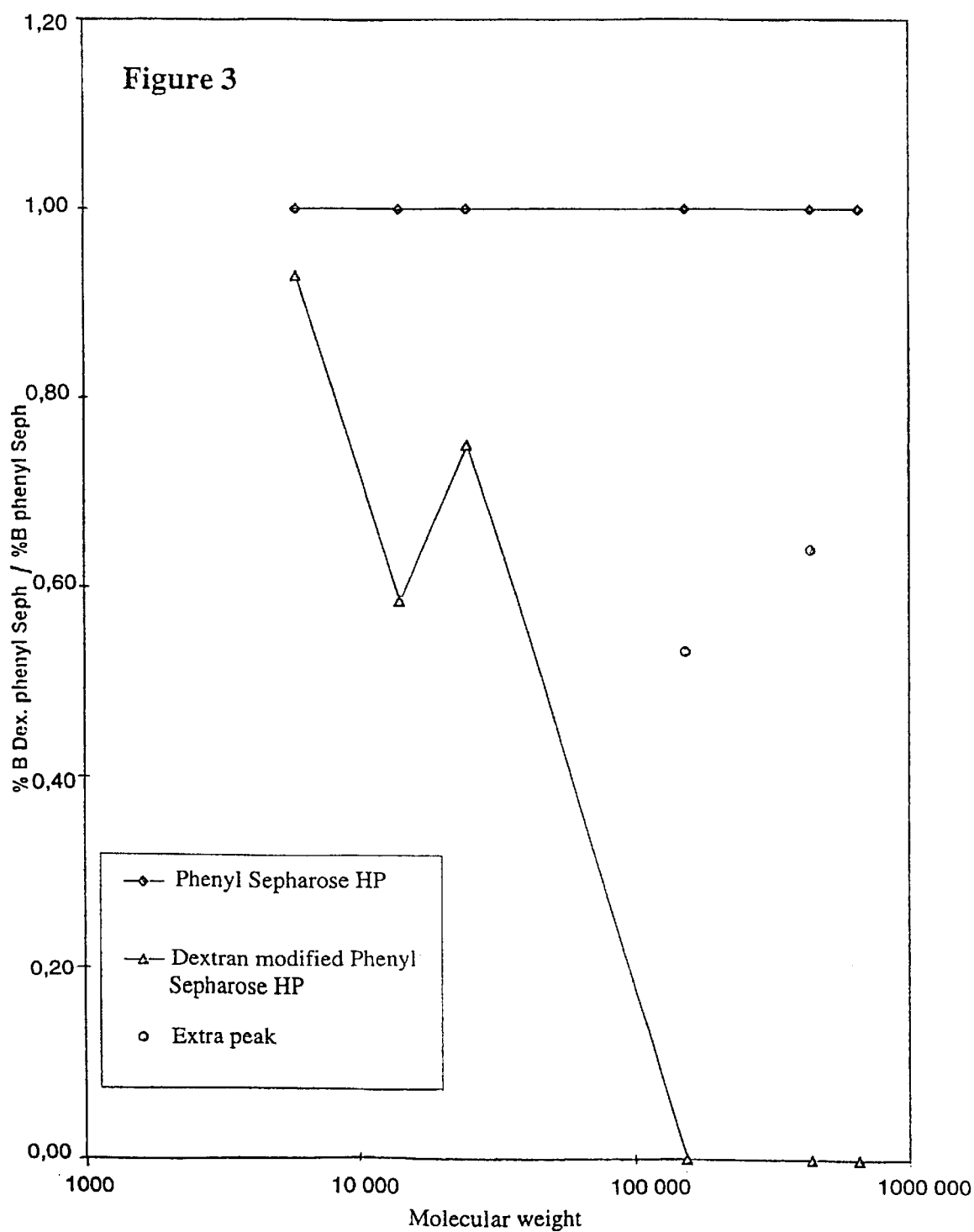

MATRICES FOR SEPARATION AND SEPARATION EXPLOITING SAID MATRICES

REFERENCE TO RELATED APPLICATIONS

This application is a 371 of PCT/SE98/00387 filed Mar. 4, 1998.

TECHNICAL FIELD

The present invention relates to matrices which can be used for separation of one or more components in a mixture of components. There are also other uses of the particular type of matrices. The separation means that a liquid containing the component(s) is contacted with the particular type of matrix, wherein the component(s) to be removed is (are) partitioned to the matrix and thereby separated from the remaining components which are differently partitioned to the matrix. By the expression "partitioned to the matrix" is meant that components bind or otherwise are adsorbed on (in) the matrix.

The separation methodology may be in form of chromatography on a monolithic matrix or on a packed or fluidized bed of particles or as a batchwise process with suspended particles. Partition to the matrix may be based on affinity or molecular size/molecular shape, such as in affinity and gelchromatography, respectively.

By separation is also meant desalting, buffer exchange, concentration and the like, wherein a separation matrix is contacted with a liquid containing something to be removed.

In the liquid containing the components to be separated, a convective mass transport occurs because of streaming or turbulence. In relation to this mass transport, matrices used for separation according to the above typically show two kind of environments: 1) an environment in which convective mass transport occurs (convective environment) and 2) an environment in which only diffusive transport occurs (diffusion environment). The two environments usually are in contact with each other via the liquid used through openings preventing convective mass transport.

Monolithic matrices and particulate matrices may show both types of environments. For monolithic matrices in the form of through flow pores and diffusion pores, respectively. A further convective environment for particles is the external environment around the particles, i.e. the void volume between the particles in the packed beds and surrounding liquid in suspensions and fluidized beds. Matrices intended for chromatography and showing both through flow and diffusion pores have probably been utilized for a long time without ability to optimally use the pore types. See, for example, WO-A-9100762 (Perseptive Biosystems Inc.). Matrices based on polysaccharides and showing both types of pores have been described in WO-A-9319115 (Pharmacia Biotech AB).

The size limit for the pores to function as through flow or diffusion pores is a consequence of the mobility an viscosity of the liquid (for example flow rate), characteristics of the pore surface, possible coating on the surface restricting the flow giving convective mass transport etc. Sizes of through flow pores which are of interest for separation purposes are within the interval 0.4–1,000 $\mu$m. The size of diffusive pores is a consequence of the same variables as those of the through flow pores. For separation purposes the diffusive pores should typically be less than 1 $\mu$m. The analogous holds also for the openings between the diffusion environment and the convective environment.

Technical Background: Advantages With the Invention and Problems Solved by the Invention.

In order to secure that a pure product is obtained, several different complementary chromatographic techniques are often used serially, e.g. gel filtration, ion exchange chromatography, hydrophobic interaction chromatography, bioaffinity chromatography. Several sequential chromatographic steps are cumbersome and costly, and especially in an industrial scale the costs may limit the ability to accomplish purification.

Many attempts have been made to create multifunctional chromatographic media in order to decrease the number of purification steps, inter alia, by providing the chromatographic materials with different functional groups giving different types of physical/chemical interactions with the substances to be purified. In practice, different interactions often counteract each other leading to an impaired result (for example a combination of electrostatic and hydrophobic interaction).

Ion exchange on particulate ion exchangers often leads to aggregation of the matrix particles in the presence of macromolecules of opposite charge compared to the particles. These problems are due to surface charges and are accentuated in batchwise suspension procedures and fluidized beds. In this context, there is especially mentioned cell culture supernatants and other sample solutions containing whole cells and/or parts thereof, including microorganisms of different types.

In the present invention, it has been possible to achieve co-operation of different separation principles on the same chromatographic medium and in this way reduce the number of necessary separation steps in a purification process.

Known Matrices

Porous particles of cross-linked agarose coated with dextran are marketed by Amersham Pharmacia Biotech AB (Uppsala, Sweden) under the designation Superdex®. In the production of Superdex®, dextran is used having a molecular weight distribution which allows the dextran to be present in interior as well as in exterior parts of the particles.

Pore surfaces in membranes/matrices can be coated with polymers of such molecular weight that clogging of the pores is prevented (EP-A-221046, Monsanto).

Multifunctional matrices of a different construction than the invention have been described previously. See U.S. Pat. No. 454,485 (Purdue University; Hagestam & Pinkerton), U.S. Pat. No. 5,522,994 (Cornell Res. Found.; & Svec), WO-A-9409063 (Cornell Res. Found.; Frechet & Svec), WO-A-9408686 (Cornell Res. Found.; Frechet, Smigol & Svec) och WO-A-9317055 (Cornell Res. Found.; Frechet & Hosoya).

OBJECT OF THE INVENTION

The objects of the invention are to provide:
1. Gel filtration media having improved selectivity with regard to the discrimination between components having different size and shape.
2. Porous particles or porous monolithic structures whose inner environment differs from their surface environment in regard to type of functional group, charge, hydrophobic/hydrophilic environment etc.
3. Simplified separation methods based on gel filtration, partition chromatography and affinity, including ion exchange, hydrophobic interaction, bioaffinity interactions/reactions etc., especially in regard to liquid chromatography.
4. New particles or monolithic structures with a surface layer inside or outside the matrix which are delimiting smaller inner pores (micropores) from larger pores (macropores) or from the surrounding of the matrix. This surface layer shall prevent compounds/components that are above a certain size from passing through and may also prevent larger compounds/components to attach to the matrix (surface layer, lock). The adsorption characteristics of the micropores may also be different from those of the surface layer so that components, penetrating into the micropores, do not adhere in/on the surface layer.

BRIEF DESCRIPTION OF THE DRAWINGS

FIG. 3 plots the lock-effect against molecular weight.

DESCRIPTION OF THE PREFERRED EMBODIMENTS

The Invention

Figure 1:
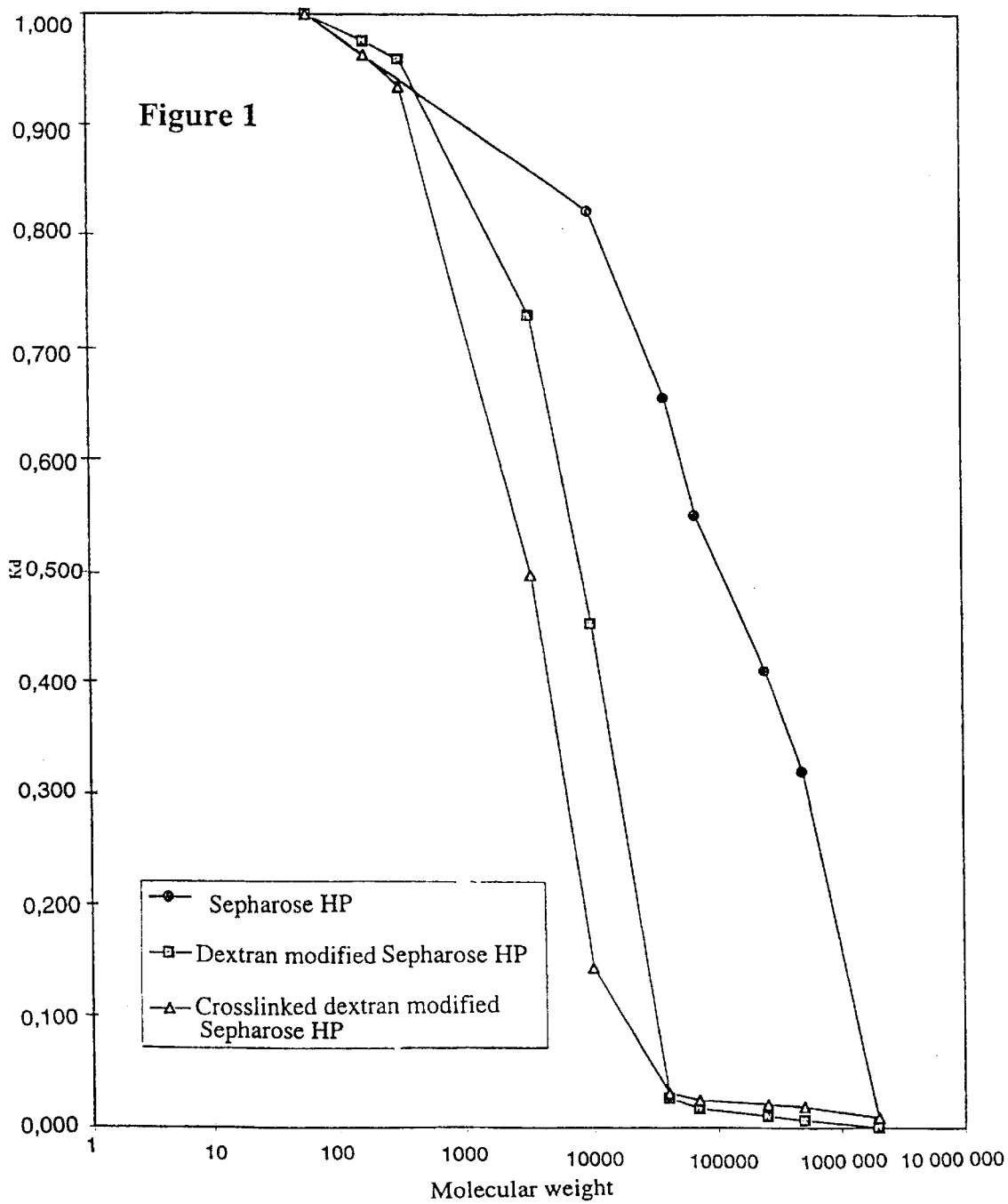
FIG. 1 plots $K_d$ against molecular weight.

The improvements of the invention are accomplished with matrices showing an inner surface defining a pore system with small pores (micropores) and an outer surface delimiting the micropore system. The characterising feature of the invention is that a polymer (I) is attached to this outer surface of the matrix (core), which polymer has such molecular weight and shape that it cannot penetrate into the micropores. Interesting micropores are in several cases smaller than 1 μm, but can also be larger, depending on the intended use of the finished matrix. The micropores correspond in many cases to diffusion pores. The outer surface can be a surface to which convective mass transport can occur. Insofar the outer surface corresponds to pore surfaces, the corresponding pores are called macropores below.

By the expression "such molecular weight and shape that it cannot penetrate into the micropores" is meant that the polymer preparation (polymer I), being exploited for coating, has a molecular weight distribution of such a kind that all or substantially all polymer molecules in the preparation are excluded from transport into the micropores, when the preparation is dissolved in a liquid which, via the micropores, can be transported into the naked matrix. This means that polymer I, when it is anchored to the outer surface, can give separation characteristics of the surface, which are different from the separation characteristics of the micropores.

Naked Matrix (the Core)

As a rule, basic matrices for chromatography and molecular sieves are suitable as cores in the invention. Such basic matrices may be monolithic or particulate, based on organic or inorganic material, based on one or more polymers, be hydrophilic, hydrophobic or intramediately hydrophilic etc.

Examples of hydrophilic organic cores are polymers showing several hydrophilic groups, such as hydroxy groups, (—OH), amine groups (primary, secondary, tertiary, quaternary amine/ammonium), carboxy groups (—COOH/—COO⁻), repeating groups —OCH$_2$CH$_2$— and —OCH$_2$CH$_2$CH$_2$—, —OCH$_2$CH$_2$(CH$_3$)—, amide groups (—CONH$_2$ possibly substituted with lower alkyl (C$_{1-10}$) etc., wherein hydrophilic groups preferably are directly bound to single monomer units in the polymer. Polyhydroxy polymers and polyamides are typical hydrophilic polymers, among which are noted polymers that are insoluble in aqueous media and based on polyvinylic alcohol, poly (hydroxyalkyl methacrylates) and corresponding acrylates, polyacryl and polymethacrylamides (e.g. trisacrylamides and trismethacrylamides (tris=(HOCH$_2$CH$_2$)$_3$CNH$_2$)), which possibly are cross-linked by N,N'-alkylene-bismethacrylamide or corresponding bisacrylamide, polysaccharides such as agarose, dextran, starch, pullulane and cellulose, which all may be cross-linked if desired. Preferred polyhydroxy polymers are typically wettable, preferably swellable, in liquid media suitable for separation, for example water. Surfaces in the pores of hydrophobic cores may be hydrophilized i.e. derivatized for exposure of one or more of the hydrophilic groups mentioned above so that water easier can penetrate the inner of the core. A number of methods for hydrophilization are previously known, for example coating with a hydrophilic polymer with ability to penetrate the micropores of the core in dissolved form (U.S. Pat. No. 4,535,010, Axén et al.; and U.S. Pat. No. 5,030,352, Regnier et al.) and to adhere to the pore surface, possibly with stabilisation via cross-linking and/or covalent binding to the surface. In alternative methods, the polymerisation to produce the core occurs in presence of a co-polymerisable monomer exhibiting a hydrophilic end (reactive tenside), or hydrophilic groups are later covalently introduced to hydrophobic groups in the basic polymer backbone. The latter can be performed by grafting/polymerization of water soluble monomers or polymer compounds to the surface.

Examples of hydrophobic organic cores are porous forms of styrene-divinyl benzene polymers, poly(alkyl methacrylates), polymers of perfluorinated hydrocarbons (PFC) etc.

Examples of inorganic cores are porous forms of glass, silica gel, zeolites, kieselguhr, composite material, zirconium oxide etc.

At filing of the present application, the most preferred cores were based on agarose in bead shape possibly cross-linked and possibly also derivatized with dextran in the pores, for example qualities marketed under the trade name Sepharose® and Superdex®, respectively, cross-linked dextran in bead shape, for example qualities marketed under the trade name Sephadex®, cellulose, for example qualities marketed under the trade name Sephacel®, cross-linked porous particles of polyacrylamide derivatized with dextran in the pores, for example Sephacryl®, and monodisperse and polydisperse porous particles of for example styrene-divinyl benzene polymer which have been hydrophilized, for example qualities marketed under the trade name Mono-Beads® and Source®. These trade marks correspond to products sold by Amersham Pharmacia Biotech AB, Uppsala, Sweden.

Polymer in Surface Layer Delimiting Micropores (polymer I).

Polymer I may either be hydrophilic, hydrophobic or intermediately hydrophilic depending on which liquid medium is to be used for the separation.

According to the invention, it is often suitable that surfaces in the pores of the core, the liquid medium and polymer I have similar hydrophilic/hydrophobic characteristics to simplify the penetration (wetting) of the inner and outer surfaces of the matrix by the liquid media. For the combination of polar liquid media, for example aqueous, with polar cores suitable as polymer I are: water soluble forms of polyvinylalcohol (PVA), dextran, cellulose, agarose, polyethers, such as polyethyleneoxide, polyproyleneoxides and their co-polymers etc. For the combination of less polar or non-polar liquid media and cores, polystyrene, hydrophobized dextran or similarly treated cellulose may be suitable as polymer I. This does not exclude the use of a combination of hydrophobic surfaces in the micropores, delimiting surface layers with hydrophilic or less non-polar polymer I and hydrophilic liquids.

Polymer I may be functionalized before it is attached on the surface delimiting the micropores. Functionalisation in this context means that polymer I is provided with the groups, present on the finished surface layer, or groups, simplifying a subsequent derivatization. Polymer I may also be in the form of colloidal particles which cannot penetrate into the micropores.

Polymer I may be based on the same or a different polymer as the one of the core (polymer II).

Polymer I may be a mixture of polymers.

After attachment of polymer I to the core, polymer I may be cross-linked or functionalised.

Porosity and Particle Size

Interesting exclusion limits (porosity) correspond to Stokes radius in the interval $3-10^6$ Å. Within the technical field of the applicant, and future patent owner, it may be advantageous if the outer layer has an exclusion limit above 10 Å. The exclusion limit is mainly chosen so that material to be separated from the mixture can penetrate the micropore system while at least some of the remaining components in a mixture are excluded. There are embodiments which are based on the reverse situation.

For some embodiments the outer layer, which is comprised of immobilized polymer I, is more dense than the micropores, i.e. less components are allowed to migrate into the matrix at the same time as larger components effectively are excluded. For other applications, the reverse may be applicable for the micropore system and the outer layer. The porosity may also be the same for the micropore system and the outer layer.

Particles exploited in the invention can have different shape, for example irregular as in crushed material or more or less spherical as beads. The sizes of the particles are chosen according to previous knowledge in the technical field. In the separation procedures according to the invention, it is thus possible to use a population of particles where the sizes vary within a certain interval with a mean value in the interval 1–10,000 $\mu$m, preferably 1–5,000 $\mu$m and most preferably 1–1,000 $\mu$m. The particles of the population may also be monodisperse having a particle size within any of these interval.

Macropores of monolithic matrices may be of a different size and shape analogous to the above discussion about particles. In such embodiments the surface of the macropores is covered by polymer I.

Density of Particlulate Matrices

Depending on the use of the finished matrix, it may exist a need for matrices having a larger, a lesser or the same density as the liquid medium in which they are intended to be used (density for matrix saturated with the liquid medium). Production of particulate matrices can be done by incorporating filling-agents, often in the form of smaller particles, in the matrices. Particulate matrices having a density deviating from the liquid medium used for separation have mostly been used for batchwise suspension procedures and for expanded/fluidized beds. Typically for this embodiments the density is over 1.02 g/cm$^3$, preferably over 1.1 g/cm$^3$, or under 0.98 g/cm$^3$. See, e.g. WO-A-9200799 (Kerm-En-Tek/Upfront Chromatography). See also WO-A-9118237 (Amersham Pharmacia Biotech AB) which also describes that large practical advantages are achieved if the used fluidized bed only is stabilized by a liquid flow. It has also been popular to use magnetic filling-agents to simplify separation of the particles and stabilisation of fluidized beds by magnetic fields.

Production of the Matrices—Coating With Polymer I

The production typically involves contacting a porous core according to the above with a liquid, which in dissolved form contains polymer I having a size and shape preventing the polymer to penetrate into micropores of a predetermined diameter. For micropore systems with large pores, polymer I can be in the form of colloidal particles. Polymer I, the core and conditions are adapted lo each other so that polymer I binds to the surfaces which delimit the micropore system.

For binding of Polymer I to the core, hydrophobic interaction can be used, as well as interactions between charged groups, between polar structures, between charged group and polar structure etc. or covalent binding. Polymer I may, if needed, be stabilised to the core via cross-linking in a subsequent step. Binding to a surface via hydrophobic or hydrophilic interaction (hydrophobic surface—hydrophobic polymer I and hydrophilic surface—hydrophilic polymer I) has, inter alia, been described in EP-A-221046 (Monsanto). Providing polymer I and the core exhibit nucleofilic groups, polymer I may bind to the core by impregnating or activating the core with a bifunctional reagent. See Axén et al. (U.S. Pat. No. 4,535,010). Examples of bifunctional reagents which can be used are CNBr, epihalohydrines, bisepoxides etc. An important variant is activation by adding halogen or corresponding hypohalite to alkene structure. Examples of groups showing alkene is "pure" allyl $CH_2=CHCH_2—$, where the free valence binds directly to the matrix, and groups where allyl binds to the matrix via a bridge ($CH_2=CHCH_2OC_6H_4—$, $CH_2=CHCH_2OCH_2CHOHCH_2—$, $CH_2=CHCH_2OC_6H_4OCH_2CHOHCH_2—$ etc.)

Especially there can be mentioned the method developed by us for layer activation/partial activation. The method comprises activation/contacting a porous matrix with a deficiency of activating reagent, which is chosen so that activation can be controlled to be faster than the transport of the reagent into the matrix. A typical example is to react a porous matrix showing alkene group with a deficient amount of halogen (in relation to alkene group). The method can be controlled to give selective activation in a surface layer, which in a subsequent step can be used to covalently bind polymer I. See our co-pending application with the title "Process to introduce a functionality", the text of which hereby is incorporated by reference (SE-9700768-6 with a corresponding International Patent Application filed concurrent with the present International Patent Application). Following the coating reaction, remaining alkene groups may be activated for incorporation of a functionality and/or cross-linking in the remaining part of the core, either in the form of layers or in the whole core. The method enables production of multifunctional chromatographic media, in which each functionality is located to a layer in the core.

Functionalisation of the Matrices

The ready matrix may contain functional groups (ligands) of the same kind as those used within liquid chromatography. Examples are:

1. ion exchange groups
2. bioaffinity groups
3. hydrophobic groups
4. groups that can be used for covalent chromatography
5. sulphur-containing groups, for example, for so called thiophilic interaction,
6. chelate or chelating groups,
7. groups with aromatic systems giving rise to so called π-π-interaction with different compounds,
8. groups giving hydrogen bonds
9. hydrophilic groups etc.

The substitution degree for at least one ligand from the groups 1–9 in the micropores is often different from the substitution degree for the same ligand in the surface layer delimiting the micropores. In many embodiments of the matrices of the invention, the substitution degree for a ligand in the surface layer is zero or close to zero, at the same time as the same ligand is present in the micropore system. Also the reverse may be at hand. Ligands chosen from the groups 1–2 and 4–8 may be absent in the surface layer.

Ion exchanging groups can be anion exchanging, such as primary, secondary, tertiary, quaternary ammonium group, sulphonium group etc., or cation exchanging, such as carboxylate (—COO$^-$), phosphonate or phosphate (—PO$_3^{2-}$, —OPO$_3^{2-}$ respectively), sulphonate or sulphate (—SO$_3^-$ and —OSO$_3^-$ respectively) etc. In the groups —COO$^-$, —PO$_3^{2-}$, —OPO$_3^{2-}$, —SO$_3^-$ and —OSO$_3^-$ the free valence binds directly to a carbon atom.

Well known bioaffinity groups are single members of the pairs a) antigen/hapten and antibody (including antigen or hapten binding fragments thereof, b) nucleic acid and its complementary counterpart, c) lectin and carbohydrate structure, d) IgG binding protein and protein showing the part of IgG binding to such protein, e) sense and antisense based affinity systems etc. Among bioaffinity groups, also groups are comprised originating from synthetically produced organic molecules, which "mimic" naturally occurring biospecific affinity, so called "mimetics".

Hydrophobic groups often are hydrocarbon groups containing few or no oxygen, nitrogen or sulphur atoms. Typical exemples of hydrophobic groups are straight, branched and cyclic saturated, unsaturated or aromatic hydrocarbon groups. Typically the groups have less than 25 carbon atoms.

Among groups which can be used for covalent chromatography there can be mentioned disulphide groups, mainly reactive disulphide groups (—S—S—R$^1$) and free thiol groups (—SH). An example of R$^1$ is 2-pyridyl. For further examples of R$^1$ see, for example, U.S. Pat. No. 4,647,655 (Pharmacia AB).

Among sulphur containing groups which can be used for thiophilic interaction there can be mentioned groups which are significantly hydrophobic but in which there are one or more thio ether structures. See, for example, Oscarsson & Porath WO-A-9533557; Porath EP-A-165912; and Porath EP-A-168363.

Hydrogen binding groups have recently been used (Belew, Berglund, Bergström, Söderberg, SE 9600590-5 (=WO 97 29825) (incorporated by reference)). This type of groups often show a weak anion exchanging ammonium group (primary, secondary or tertiary) with a hydroxy group at a distance of 2 or 3 carbons from the ammonium nitrogen.

Hydrophilic groups according to the invention are mainly single hydroxy, lower hydroxy alkyl with one or more hydroxy groups, groups containing repeating structures —CH$_2$CH$_2$O— etc. The groups often are of low molecular weight, for example, with less than 25 carbon atoms.

Hydrophilic or hydrophobic polymer groups with or without ligands can give gel filtration characteristics. The polymers of this type of group may be cross-linked.

Suitable groups (ligands) are typically coupled to the matrix via a bridge which may have a structure selected according to known techniques. The bridge structure may be polymeric, for example hydrophilic or hydrophobic polymer, having one or more of the groups 1–10 according to the above on each linker. Common bridge names have been "spacers", "tentacles", "extenders", "fluff", "linkers" etc., each of which sometimes has a certain meaning. Hydrophobic bridges are mainly suited for hydrophobic liquid media and, if they are polymeric, often lead to better availability and capacity for introduced groups 1–9. The corresponding is true for hydrophilic bridges in combination with hydrophilic liquid media. Examples of hydrophilic polymer bridges are polysaccharides such as dextran and other water-soluble polyhydroxy polymers. Polymer bridges can be used to create matrices with gel filtration characteristics.

Utility

The main utility of the matrices is separation of the kind mentioned in the introduction. The mentioned exclusion limits and functional groups enable use of the matrices according to the invention for separation of nucleic acid, proteins including peptides and other organic and inorganic compounds. The separation may be performed from mixtures containing similar or very different components, everything from single small molecules up to complex entities, such as particulate aggregates, bioaffinity complexes, animal and plant cells and parts thereof, microorganisms and parts thereof etc.

The matrix which is contacted with a liquid medium can be monolithic or in the form of a bed of packed particles, wherein the liquid medium is allowed to pass through the matrix (chromatography). If the matrix consists of particles these can alternatively be suspended, for example by stirring or fluidizing by a liquid flow such as in an expanded bed. For suspensions batchwise procedures are perfomed. For fluidized stable beds, the separation can be performed as chromatography (WO-A-9218237, Pharmacia Biotech AB).

The separation, depending on choice of matrix and substituting group (see above), can be designed as affinity chromatography or as chromatography based on the size of the particular compounds and the shape thereof (gel chromatography) or as corresponding batchwise procedures. Examples of affinity chromatography are ion exchange chromatography (anion exchange, cation exchange), bioaffinity chromatography, hydrophobic interaction chromatography (HIC), covalent chromatography, thiophilic chromatography, chelate based chromatography, chromatography based on π-π-interaction, etc. In principle, conditions and protocols are chosen in accordance with previous knowledge for the respective type of separation procedure.

The invention will now be presented with a number of practical examples which by no means are restricting in relation to the general application of the invention. The invention is defined in the enclosed patent claims and in the description.

PATENT EXAMPLES

Example 1

Cross-linked Allylated Agarose in Particle Shape Coated With Raw Dextran

A. Production of cross-linked allylated agarose in particle shape Cross-linked agarose (34 μm particles) produced by a reaction between epichlorohydrin and agarose in the presence of NaOH according to Porath et al. (J. Chromatog. 60 (1971) 167–77 and U.S. Pat. No. 3,959,251) was reacted with allylglycidyl ether with NaOH as a base to an allyl level (CH$_2$=CHCH$_2$OCH$_2$CHOHCH$_2$—) of 0.21 mmole/mL gel. In aqueous media we have succeeded to produce gels with an allyl level in the interval 0.005–0.450 mmole/mL gel. If the reaction is performed in organic solvents even higher substitution degrees can be obtained.

B. Dissolving of raw dextran. Raw dextran is a non-hydrolyzed dextran from Leuconostoc mesenteroides with ultrahigh molecular weight, often between 10–30 million Dalton. Following purification with repeated ethanol precipitations, raw dextran is in principle completely free from low molecular sugar compounds. The raw dextran that was used was from Amersham Pharmacia Biotech's production plant in Staffanstorp, Sweden. 47.5 g ethanol precipitated and freeze dried raw dextran was dissolved in 230 mL distilled $H_2O$ in a 1,000 mL three-necked flask under slow stirring.

C. Bromination of cross-linked allylated agarose. 200 mL drained allylated agarose produced according to step A, 200 mL distilled water and 5.72 g NaOAc were added to a 1,000 mL three-necked flask. Thereafter, bromination occurs by dripping in an excess of bromine water. Sunbsequent to bromination the gel is washed on a glass filter with distilled water.

D. Coupling reaction: The gel from step C is aspirated dry and transferred to the flask containing dissolved raw dextran from step B during careful stirring. The mixture is allowed to equilibrate for one hour. Thereafter the reaction is started by addition of 29.2 g NaOH and 0.73 g $NaBH_4$ dissolved in 91 mL distilled $H_2O$. The temperature is set to 50° C. and the reaction is allowed to proceed over night (for example 16 h) and then the reaction is stopped by neutralisation with concentrated HOAc in the reaction vessel to a pH below 7, preferably 5–6. Thereafter, the mixture is filtered on a glass filter and washed with distilled water.

Example 2

Cross-linking of Particle Used in Example 1. Cross-linker 1,4-Butanediol Diglycidyl Ether 44.8 g of particles according to example 1 coated with raw dextran are weighed in dry aspirated form in a previously calibrated plastic meter glass, and then the volume is adjusted with distilled water to 75 mL (total water and gel). The mixture is then transferred to a 250 mL three-necked round flask to which is added 15 mL 1,4-butanediol diglycidyl ether at room temperature. Thereafter, 35.0 mL of 11 M KOH (0.385 mole) is added to the vessel by pumping at 0.3 mL/min (start). This takes about 2 hours. The temperature of the thermostat is set to 40° C. Stirring. The reaction is allowed to proceed over night (about 16 hours) and is stopped by neutralisation with conc. HOAc to a pH below 7, preferably 5–6, after which the mixture is filtered on a glass filter and finally the gel is washed with distilled water.

Example 3

Phenyl Sepharose HP Coated With High Molecular Weight Dextran

A. Production of phenyl substituted cross-linked allylated agarose (allylated Phenyl Sepharose HP): Phenyl Sepharose HP is commercially available from Amersham Pharmacia Biotech AB. It consists of phenylated cross-linked agarose (34 µm particles). Allylation is achieved by reacting the finished particle with allylglycidyl ether with NaOH as a base to an allyl level ($CH_2=CHCH_2OCH_2CHOHCH_2-$) of 0.17 mmole/mL.

B. Dissolving of raw dextran: 53.5 g of ethanol precipitated and freeze dried raw dextran is dissolved in 325 mL distilled water in a 1,000 mL flask with slow stirring.

C. Bromination of allylated Phenyl Speharose HP: 250 mL allylated Phenyl Sepharose HP produced in step A, 250 mL distilled water and 5.23 g NaOAc (anhydrous) are added to a 1,000 mL three-necked round flask. Thereafter, an excess of elementary bromine is added by dripping to achieve bromination, and then the gel is washed on a glass filter with distilled water.

D. Coupling reaction: The gel from step C is aspirated dry and transferred to the flask containing dissolved raw dextran from step B. The mixture is allowed to equilibrate with careful stirring. Thereafter the reaction is started by addition of 36.5 g NaOH and 0.95 g $NaBH_4$ dissolved in 114 mL of distilled water. The temperature is set to 35° C. and the reaction is allowed to proceed over night (16 h) under careful stirring. The reaction is then stopped by pouring off the reaction mixture in a 2 liter beaker and neutralisation with concentrated HOAc to pH<7, preferably 5–6. Finally the gel is washed with distilled water on a glass filter.

Example 4

Q Sepharose HP Coated With High Molecular Dextran

A. Production of allylated Q substituted cross-linked agarose (allylated Q Sepharose HP): Q Sepharose HP is commercially available from Amersham Pharmacia Biotech AB. It consists of cross-linked agarose (30 µm particles) which is substituted with quaternary groups $(CH_3)_3N^+CH_2CHOHCH_2-$ with ion exchanging capacity of 0.15–0.20 mmole/mL gel). Allylation occurs by reacting the finished particle with allylglycidyl ether with NaOH as a base to an allylic level ($CH_2=CHCH_2OCH_2CHOHCH_2-$) of 0.088 mmole/mL.

B. Dissolving of raw dextran: 4.28 g of ethanol precipitated and freeze dried raw dextran according to the above are dissolved in 26.0 mL distilled water in a 100 mL three-necked flask under slow stirring.

C. Bromination of allylated Q Sepharose HP: 20 mL Q Sepharose HP produced in step A (substitution degree allyl groups 0.088 mmole/mL), 20 mL distilled water and 0.26 g of anhydrous NaOAc are added to a 100 mL three-necked round flask. Thereafter, bromine water in excess is dripped in to achieve bromination, and then the gel is washed with distilled water on a glass filter.

D. Coupling reaction: The gel from step C is aspirated dry and transferred to the flask containing dissolved dextran. At the same time, 5.51 g PEG 35000 (Polyscience Inc., Warrington, Pa., USA) is added under careful stirring. The mixture is left for equilibration under careful stirring for about 1 hour. Thereafter, the reaction is started by addition of 2.92 g NaOH and 0.08 g $NaBH_4$ dissolved in 9.12 mL distilled water. The temperature is set to 35° C. and the reaction is allowed to proceed over night (about 16 h) under careful stirring. The stirring is stopped and the reaction mixture filtered on a glass filter. After the raw dextran has been washed away with distilled water, neutralisation is performed with a few mL concentrated HOAc directly in the filter funnel to pH<7, preferably 5–6, whereupon the gel is washed again with distilled water.

Example 5

Gel Filtration, Cross-linked Agarose Modified With Raw Dextran, With or Without Subsequent Cross-linking Particles according to example 1 and example 2 are compared with unmodified beads by testing their gel filtration characteristics. The gels are packed in HR 10/30 columns from Amersham Pharmacia Biotech AB. 1% solutions of dextran were used as samples. Raw dextran was used as a void marker and ethylene glycol as a total volume marker ($V_0+V_t$). 100 µL was injected of respective sample. The samples were eluated in separate runs with distilled water at a flow of 1 mL/min. and detected by a flow refractometer.

$K_d=[V_e-V_0)/V_i]$ was calculated and plotted against molecular weight in a lin-log diagram, see FIG. 1. Circles stand for unmodified particles, squares stand for particles modified with raw dextran and triangles stand for particles modified with raw dextran and then cross-linked.

The selectivity is markedly changed when modification is performed with raw dextran. The selectivity curve, $K_d$=f[log (molecular weight)] becomes steeper and is considerably biased against lower molecular weights. The exclusion limit decreases to just below 100,000 daltons. Cross-linking of the bound raw dextran contributes to further biasing of the selectivity curve towards lower molecular weights, $K_d$ values decrease further.

Example 6

Ion Exchange, Raw Dextran Modified Q-Sepharose HP

Q-Sepharose HP (Amersham Pharmacia Biotech AB) modified according to example 4 was packed in HR 5/5 columns from Amersham Pharmacia Biotech AB to a bed height of about 5 cm. Gradient chromatography was performed on a FPLC system provided with measuring cells for $UV_{280}$ and conductivity with the following conditions:

| | |
|---|---|
| Buffer A) | 20 mM Tris-HCl pH 8.2 |
| Buffer B) | 20 mM Tris-HCl pH 8.2 + 0.5 M NaCl |
| Flow rate | 1.0 mL/min. |
| Gradient volume | 20 mL |
| Samples | Thyroglobulin, Ferritin, IgG. CO-Hb, EGF and in certain cases transferrin |
| Sample conc. | About 1 mg/mL in buffer A |
| Sample volume | 50 µL |

The elution concentration at peak maximum was determined for unmodified Q-Sepharose HP and Q-Sepharose HP modified with raw dextran. A dimension-less value on the lock-effect was calculated as the quotient between the elution concentrations for Q-Sepharose HP modified with raw dextran and unmodified Q-Sepharose HP, respectively. This quotient is a measure of the ability of the sample to penetrate the outer raw dextran layer and interact with the inner of the bead, the lock-effect. The value 0 means that the sample is completely excluded and that no ionic interaction occurs. The value 1.0 is obtained when the interaction is identical with the interaction with unmodified Q-Sepharose HP ion exchanger.

Figure 2:
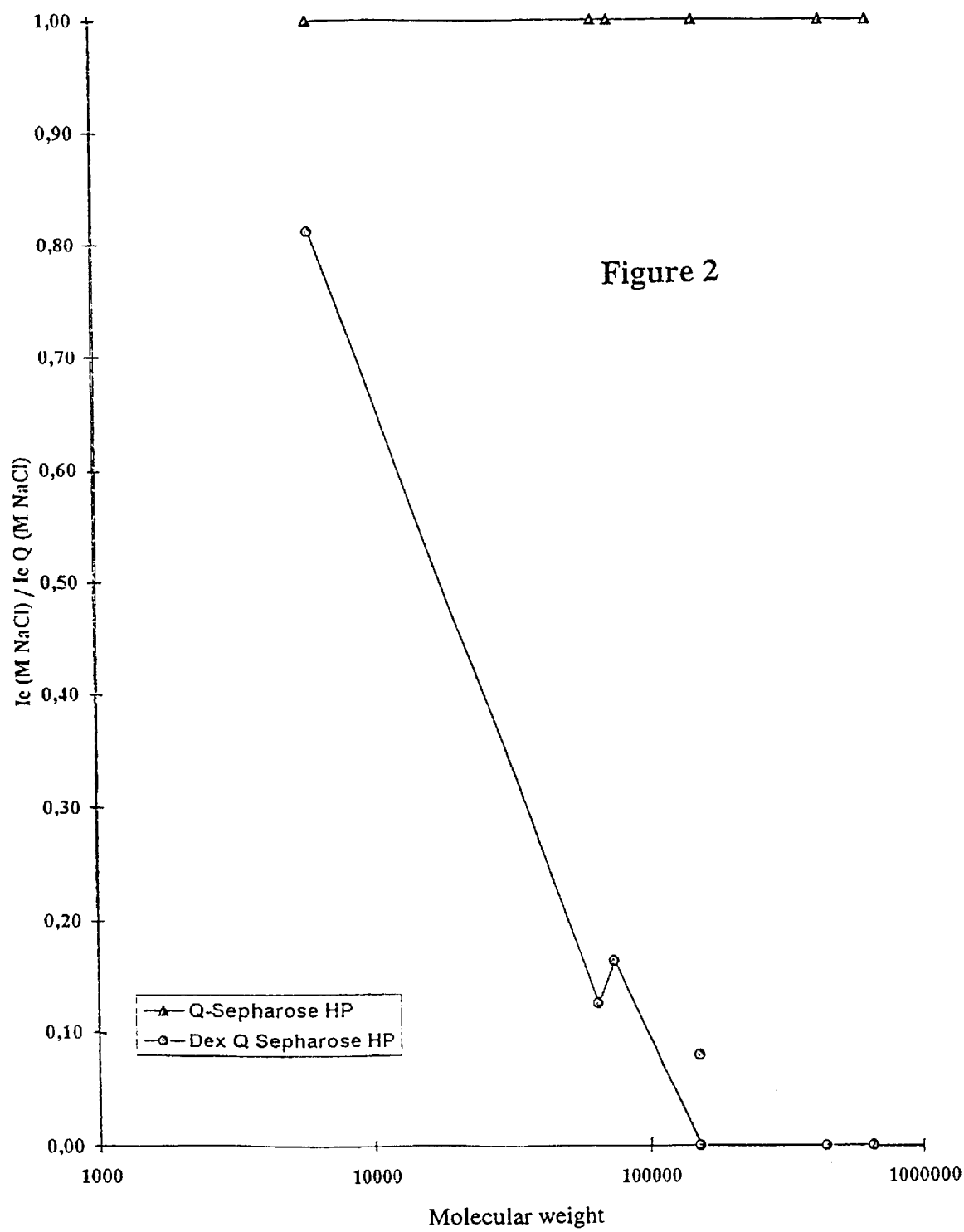
FIG. 2 plots the lock-effect against molecular weight.

In FIG. 2, the lock-effect has been plotted against molecular weight for the used test proteins in a lin-log diagram. In the diagram it appears that proteins having a molecular weight close to 100 kD are strongly influenced and at molecular weights just above 100 kD the proteins are not at all bound to the ion exchanger.

Example 7

Hydrophobic Interaction Chromatography (HIC)

Phenyl Sepharose HP modified with raw dextran Phenyl Sepharose HP modified according to example 4 was packed in HR 5/5 columns (Amersham Pharmacia Biotech AB) to a bed height of about 5 cm. The chromatographic runs were perfomed on a FPLC system provided with measuring cells for $UV_{280}$ and conductivity.

Large proteins are often stronger adsorbed than small proteins to unmodified Phenyl Sepharose HP. This is due to a co-operative effect which arises because a larger protein can contain more hydrophobic functional groups than a smaller one. The concentration of phosphate buffer was kept low to be able to eluate also larger proteins.

Ammonium sulphate, per se, gave a significant UV-signal and therefore a blank value was measured for each gel and was subtracted from the values for the chromatograms before they were evaluated. The elution values (% B), were calculated from the retention time of the peak after compensation for dead volume in the tubes and mixers. These values were standardized as in the above ion exchange case by division with the corresponding value for the protein on Phenyl Sepharose HP, the lock-effect, and were plotted in a diagram against the molecular weight of the protein.

The chromatographic runs in FIG. 3 were performed on a FPLC system provided with measuring cells for $UV_{280}$ and conductivity with the following conditions:

| | |
|---|---|
| Buffer A) | 10 mM $H_3PO_4$—KOH and 2.0 M $NH_4SO_4$ pH 7.0 |
| Buffer B) | 10 mM $H_3PO_4$—KOH pH 7.0 |
| Flow rate | 1.0 mL/min. |
| Gradient volume | 20 mL |
| Samples | Thyroglobulin 660 kD, ferritin 443 kD, IgG 152 kD, chymotrypsinogen A 25 kD, lysozyme 14.3 kD, EGF 6 kD, |
| Sample conc. | 1 mg/mL except for EGF 0.16 mg/mL |
| Sample volume | 50 µL |

From FIG. 3, it appears that the adsorption and elution performance on raw dextran modified Phenyl Sepharose HP markedly deviates from the unmodified Phenyl Sepharose HP. The largest deviations are obtained for larger proteins. Large molecules, such as IgG are excluded, from the hydrophobic phenyl groups present in the interior of the beads and are directly eluted without adhering to the matrix. Small molecules like EGF, lysozyme and chymotrypsinogen A enter into the particles and are adsorbed. IgG and ferritin provide two peaks probably due to that the samples also contained low molecular weight material.

Non-used killed coupling groups (for example $CH_2OH$—$CHOHCH_2$—) in the interior of the matrix provide an exclusion effect, which decreases the availability of the phenyl groups and affects the elution of the molecules which are adsorbed in the interior of the bead.

FIG. 1. Gel filtration, $K_d$=f[log(molecular weight)] for Sepharose HP modified with raw dextran without and with a subsequent cross-linking.

FIG. 2. Ion exchange, lock-effect=f[log(molecular weight)] Q-Sepharose HP modified with raw dextran.

FIG. 3. Hydrophobic interaction chromatography (HIC), lock-effect=f[log(molecular weight)] Phenyl Sepharose HP modified with raw dextran. 10 mM pH 7 ammonium sulphate 2.0–0 M.

What is claimed is:

1. A multifunctional matrix comprising a core showing a micropore system and a surface in which the micropore system has openings, said surface delimiting said openings, wherein the surface is covered with a polymer (I) having a large molecular weight preventing said polymer (I) from penetrating into the micropore system, said polymer (I) having different functional groups than the micropore system and wherein a material to be separated from a mixture can penetrate the micropore system while at least some of the remaining components in the mixture are excluded.

2. The matrix according to claim 1, wherein the diameter of the openings is less than 1 µm.

3. The matrix according to claim 1, wherein the micropore system represents a diffusive pore system with openings preventing convective mass transport into the system.

4. The matrix according to claim 1, wherein the surface in the micropores and polymer I are hydrophilic.

5. The matrix according to claim 1, wherein the surface in the micropores show hydroxy groups.

6. The matrix according to claim 1, wherein the polymer I has been cross-linked and/or covalently bound to the surface in which the micropore system has openings.

7. The matrix according to claim 1, wherein the core is built of a polymer (II).

8. The matrix according to claim 7, wherein the polymer II is hydrophobic and that its surfaces have been hydrophilized.

9. The matrix according to claim 1, wherein at least one of polymer I and II is a hydrophilic polymer.

10. The matrix of claim 9, wherein said hydrophilic polymer is a polyhydroxypolymer.

11. The matrix of claim 10, wherein said polyhydroxypolymer is a polysaccharide.

12. The matrix of claim 10, wherein said polyhydroxypolymer is cross-linked.

13. The matrix according to claim 1, wherein at least one of polymer I and II are selected from the group consisting of pullulane, starch, cellulose, dextran and agarose.

14. The matrix according to claim 13, wherein the micro pores are more difficult to penetrate than the surface which is coated with polymer I.

15. The matrix according to claim 1, wherein the surface, showing polymer I, and the micropore system in the core have different densities in relation to penetration ability by compounds with a certain molecular weight or shape, or a certain molecular weight and shape.

16. The matrix according to claim 15, wherein the micro pores are easier to penetrate than the surface which is coated with polymer I.

17. The matrix according to claim 1, wherein the micropores or polymer I, or the micropores and polymer I, show at least one ligand selected from the group consisting of a. ion exchanging groups, b. bioaffinity groups, c. hydrophobic groups, d. groups which can be exploited for covalent chromatography, e. chelate or chelating groups, f. groups with aromatic systems which can be exploited for so called $\pi$-$\pi$-interaction, g. hydrogen binding groups, and h. hydrophilic groups.

18. The matrix according to claim 17, wherein the substitution degree for at least one of the selected ligands in the micropores is different from the substitution degree for the same ligand in the surface layer which is built of polymer I.

19. The matrix according to claim 17, wherein the substitution degree for at least one of the selected ligands in the micropores or in polymer I is substantially 0.

20. The matrix according to claim 1, wherein said matrix is in the form of a set of particles whose particle size is in the interval 1–10,000 $\mu$m.

21. The matrix according to claim 20, wherein the particles when filled with a liquid medium, have a density which is distinct from that of the liquid medium.

22. The matrix according to claim 20, wherein said matrix is monodisperse.

23. The matrix according to claim 20, wherein the particles represent sizes or densities, or sizes and densities, within an interval.

* * * * *